United States Patent
Gloss et al.

(10) Patent No.: US 9,545,472 B2
(45) Date of Patent: Jan. 17, 2017

(54) EXTRACORPOREAL BLOOD CIRCUIT RESERVOIR WITH ANGLED VENOUS INLET LUER PORT

(75) Inventors: Michael Gloss, Minneapolis, MN (US); Eric Boone, St. Michael, MN (US); Neil Nye, Brooklyn Park, MN (US); Hanam Pham, Brooklyn Park, MN (US)

(73) Assignee: Medtronic, Inc., Minneapolis, MN (US)

(*) Notice: Subject to any disclaimer, the term of this patent is extended or adjusted under 35 U.S.C. 154(b) by 786 days.

(21) Appl. No.: 13/411,363

(22) Filed: Mar. 2, 2012

(65) Prior Publication Data
US 2013/0231601 A1    Sep. 5, 2013

(51) Int. Cl.
A61M 37/00    (2006.01)
A61M 1/36    (2006.01)

(52) U.S. Cl.
CPC ......... A61M 1/3627 (2013.01); A61M 1/3632 (2014.02)

(58) Field of Classification Search
USPC ........... 422/44–48; 604/6.09, 6.1, 6.14, 6.15, 604/6.16
See application file for complete search history.

(56) References Cited

U.S. PATENT DOCUMENTS

| | | | |
|---|---|---|---|
| 4,422,939 A | 12/1983 | Sharp et al. | |
| 4,642,089 A | 2/1987 | Zupkas et al. | |
| 4,781,686 A * | 11/1988 | Erickson | 604/118 |
| 4,818,490 A * | 4/1989 | Carson et al. | 422/46 |
| 5,158,533 A | 10/1992 | Strauss et al. | |
| 5,304,164 A * | 4/1994 | Lindsay | 604/403 |
| 5,411,705 A | 5/1995 | Thor et al. | |
| 5,630,946 A * | 5/1997 | Hart et al. | 210/805 |
| 5,770,073 A | 6/1998 | Bach et al. | |
| 5,823,986 A | 10/1998 | Peterson | |
| 6,981,969 B2 * | 1/2006 | Chavez et al. | 604/523 |
| 6,981,977 B2 * | 1/2006 | Herweck et al. | 606/153 |
| 7,147,614 B2 | 12/2006 | Fini | |
| 7,189,352 B2 * | 3/2007 | Carpenter et al. | 422/45 |

(Continued)

FOREIGN PATENT DOCUMENTS

| | | |
|---|---|---|
| GB | 2022434 | 12/1979 |
| WO | WO91/13640 | 9/1991 |

(Continued)

OTHER PUBLICATIONS

US 6,197,009, 03/2001, Steg (withdrawn)

*Primary Examiner* — Tatyana Zalukaeva
*Assistant Examiner* — Ariana Zimbouski

(57) ABSTRACT

An extracorporeal reservoir device including a housing, a venous inlet sub-assembly, and a venous filter. The venous sub-assembly is mounted to the housing and includes a downtube and a luer port connector body. The connector body extends from the downtube and forms a passageway open to a lumen of the downtube. The connector body is arranged such that fluid flow from the passageway merges with a flow path of fluid along the primary lumen at an angle of less than 90°. Secondary blood flow through the port connector body is less likely to induce turbulent flow into venous blood flow within the downtube, and is thus less likely to break up any bubbles carried by the venous blood. For example, at port flow rates of less than 500 mL/minute, fluid flow from the port connector body does not induce turbulent flow into fluid flowing through the primary lumen.

20 Claims, 9 Drawing Sheets

(56) References Cited

U.S. PATENT DOCUMENTS

| 7,682,563 B2 | 3/2010 | Carpenter et al. |
| 2005/0118059 A1 | 6/2005 | Olsen et al. |
| 2009/0012443 A1 | 1/2009 | Ghelli et al. |
| 2010/0011557 A1* | 1/2010 | Hopper et al. ................. 29/428 |
| 2010/0211028 A1* | 8/2010 | Wendler et al. .............. 604/317 |
| 2010/0268148 A1 | 10/2010 | Wendler et al. |

FOREIGN PATENT DOCUMENTS

| WO | WO93/11808 | 6/1993 |
| WO | WO97/33672 | 9/1997 |
| WO | WO98/20957 | 5/1998 |

\* cited by examiner

EXTRACORPOREAL BLOOD CIRCUIT RESERVOIR WITH ANGLED VENOUS INLET LUER PORT

BACKGROUND

The present disclosure relates to blood reservoirs for extracorporeal blood circuits. More particularly, it relates to blood reservoirs combining blood flows from a primary venous source and an auxiliary source and useful with various perfusion systems.

In many surgical procedures, the functions of the heart and lungs are performed outside the body by specialized devices, such as membrane oxygenators, cardiac assist pumps, and heat exchangers. This array of equipment is operated by a perfusionist who supervises the removal and return of the patient's blood during the surgical procedure. The patient's blood is stored in a venous reservoir, interposed between the vena cava tap and the pump of the heart-lung machine, which pumps the blood through the oxygenator and back into the patient's aorta. The venous reservoir also serves as a fluid buffer in the external circulation system to smooth out variations between the blood flow available from the vena cava and the demands of the heart-lung machine pump. Cardiotomy blood is also recovered, treated (e.g., filtration of surgical field debris), and returned to the patient. The venous blood and the cardiotomy blood can be separately maintained, or can be combined into a single, hard shell cardiotomy and venous reservoir.

Conventional cardiopulmonary bypass uses an extracorporeal blood or perfusion circuit that is coupled between the arterial and venous cannulae and includes a venous drainage or return line, a venous blood reservoir (or combination cardiotomy and venous blood reservoir), a blood pump, an oxygenator, an arterial filter, and blood transporting tubing or "lines". It is necessary to minimize the introduction of air into blood in the extracorporeal blood circuit, and to remove any air that does accumulate before the filtered and oxygenated blood is returned to the patient to prevent injury. In this regard, a key parameter measured by clinicians is the count and volume of gaseous microemboli (GME). GME performance is used to characterize the efficacy of a disposable perfusion circuit, where lower GME volume translates into superior air handling ability.

There are several ways that air can be introduced into the perfusion circuit before or at the circuit's reservoir. For example, air can be introduced from the venous cannula due to physician error or case complications. Also, air can be introduced through suction devices that empty into inlets of the circuit reservoir. Along the same lines, air can be introduced into the blood by turbulent flow within the reservoir. Conventional perfusion circuits incorporate various components or component designs to remove this air. For example, the reservoir can be designed to accumulate and purge larger air bubbles. Also, filters can be added to the circuit and/or be incorporated into the reservoir itself for removing GME and other particles. Thus, air introduced through the cannula may be easily separated from the blood when it enters the reservoir by simply allowing the large bubbles to float to the surface of the reservoir and dissipate into the atmosphere. However, if the bubbles at or immediately before the reservoir from the cannula are broken up, for example, by turbulent flow or sharp edges, they will lose their buoyancy and have the risk of passing through the reservoir filtration media. As a point of reference, venous filtration media is typically sized between 38 microns and 150 microns. So long as the air from the venous cannula is larger than the venous filtration media size, there is a good chance the bubbles will not pass through the media. If the air does not pass through the venous filtration media, there will be good GME performance. If the air from the venous cannula is broken into small bubbles, there is a good chance the air will pass through the venous filtration media, resulting in poor GME performance.

With the above in mind, conventional perfusion reservoir devices (either a standalone venous reservoir or a combined cardiotomy and venous reservoir) employ a "downtube" fluidly connected to the venous cannula and emptying venous blood into a chamber of the reservoir for treatment by the venous filtration media. Due to the large number of fluid connections associated with most extracorporeal blood circuits, the reservoir will conventionally incorporate a plethora of additional inlet ports. To save on space, blood flow from one or more auxiliary circuit components are commonly merged with the venous blood flow through the downtube via a luer port formed directly with the downtube. For example, a continuous one-way purge line originating from the top of an arterial filter device is connected to the venous reservoir downtube (either directly or via a separate blood sampling manifold). By allowing a continuous flow of approximately 200 mL/minute to drain from the top of the arterial filter to the reservoir, it serves as an air purge from the arterial filter. This one-way purge line prevents the accidental injection of air into the systemic side of the circuit that might otherwise occur during blood sampling or drug injection. Blood flow from other circuit components, such as an oxygenator air purge, hemoconcentrator, etc., may also be connected to the reservoir downtube's luer port(s). Regardless, luer ports traditionally are placed on the reservoir downtube at a 90° angle. When blood flow through the luer port is directed or merged into the primary venous flow through the downtube, turbulent flow is created. In instances where the primary venous blood flow includes bubbles, this turbulent flow may break up the bubbles into smaller forms, leading to the potential concern described above.

In light of the above, a need exists for an extracorporeal blood circuit reservoir device configured to merge auxiliary blood flow with primary venous blood flow in a manner that does not induce turbulent flow.

SUMMARY

Some aspects in accordance with principles of the present disclosure relate to an extracorporeal blood circuit reservoir device including a housing, an exit port, a venous inlet sub-assembly, and a venous filter. The housing defines a main chamber. The exit port is fluidly connected to the main chamber. The venous inlet sub-assembly is mounted to the housing and includes a downtube and a luer port connector body. The downtube forms a primary lumen extending between, and open relative to, opposing inlet and outlet ends. The downtube further defines an inlet section adjacent the inlet end and an outlet section adjacent the outlet end. The luer port connector body extends from the inlet section and forms a passageway that is open to the primary lumen at a flow opening. In this regard, the port connector body is arranged relative to the inlet section such that a flow path of fluid flow from the passageway into the primary lumen merges with a flow path of fluid along the primary lumen at an angle of less than 90°. Upon final construction, the venous inlet sub-assembly is arranged to locate the inlet section and the luer port connector body outside of the housing, and the outlet section within the housing. Finally, the venous filter is maintained within the housing fluidly between the outlet end of the downtube and the exit port. With this construction, blood flow through the luer port connector body is less likely to induce turbulent flow into venous blood flow within the downtube, and is thus less likely to break up any bubbles carried by the venous blood. For example, in some embodiments, at port flow rates of less than 500 mL/min through the passageway, fluid flow from the port connector body does not induce turbulent flow into fluid flowing through the primary lumen. In yet other embodiments, an extension angle defined at an intersection of an axial centerline of the passageway with a central axis of the primary lumen is less than 90°, in some embodiments in the range of 0°-85°. In yet other embodiments, the venous inlet sub-assembly further includes a second luer port connector extending from the inlet section and forming a passageway, with a flow path of fluid flowing from the passageway to the second port connector body into the primary lumen merging with a flow path of the fluid flow along the primary lumen at an angle of less than 90°. In yet other embodiments, the reservoir device is a combination cardiotomy and venous reservoir.

Yet other aspects of the present disclosure relate to an extracorporeal blood circuit including a venous cannula, a reservoir device, an arterial filter device, and an arterial cannula. The venous cannula is configured for cannulation to a patient to receive venous blood from the patient. The reservoir device includes a housing, an exit port, a venous inlet sub-assembly, and a venous filter. The exit port is fluidly connected to a main chamber of the housing. The venous inlet sub-assembly includes a downtube and a luer port connector body. The downtube forms a primary lumen extending between an opening at opposing, inlet and outlet ends. The downtube further defines an inlet section adjacent the inlet end and an outlet section adjacent the outlet end. The luer port connector body extends from the inlet section and forms a passageway that is open to the primary lumen at a flow opening. The venous filter is maintained within the housing fluidly between the outlet end and the exit port. The arterial filter device includes a purge port and is fluidly connected to the exit port downstream of the reservoir device. The purge port is fluidly connected to the luer port connector body. Finally, the arterial cannula is configured for cannulation to a patient downstream of the arterial filter. With this construction, a primary venous flow path is established from the venous cannula and through the downtube, and an auxiliary flow path is established from the purge port and through the port connector body. Finally, the auxiliary flow path merges with the primary venous flow path along the inlet section at an angle of less than 90°.

Yet other aspects of the present disclosure relate to a method of collecting and treating extracorporeal blood of a patient during a surgical procedure. The method includes directing venous source blood from the patient into an inlet end of a downtube having an outlet end. Auxiliary source blood is directed into the downtube at a location upstream of the outlet end via a luer port connector body. In this regard, the auxiliary blood source flow merges with the venous source blood flow at an angle that is less than 90°. A combination of the venous source blood and the auxiliary source blood is dispensed from the outlet end into a reservoir chamber. The combination blood is guided through a venous filter within the chamber. With this construction, the combination blood is treated by the venous filter, with large bubbles carried by the venous source blood remaining intact as the venous source blood merges with the auxiliary source blood.

DETAILED DESCRIPTION

Figure 1A:
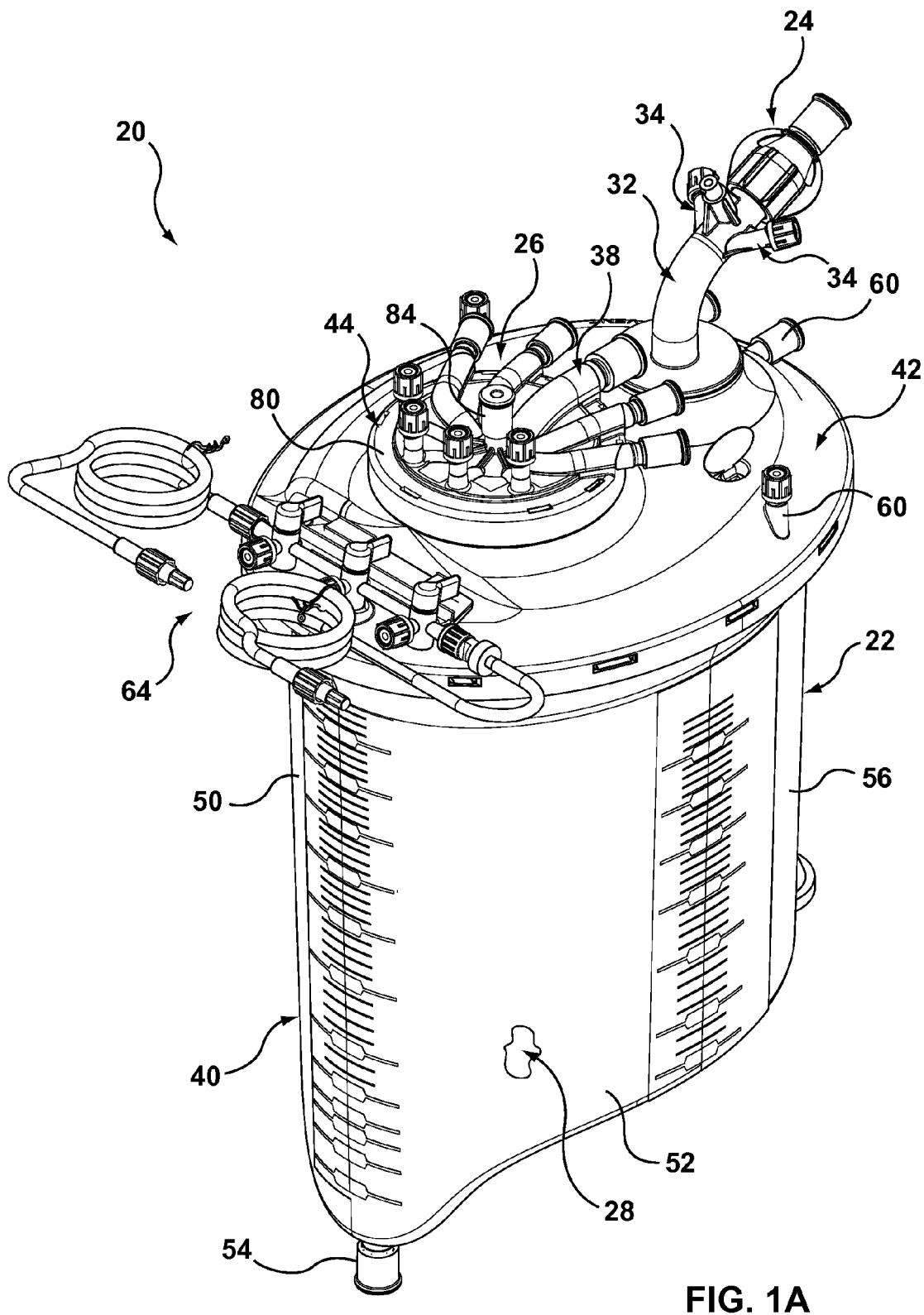
FIG. 1A is a perspective view of an extracorporeal blood reservoir device in accordance with principles of the present disclosure.
Figure 1B:
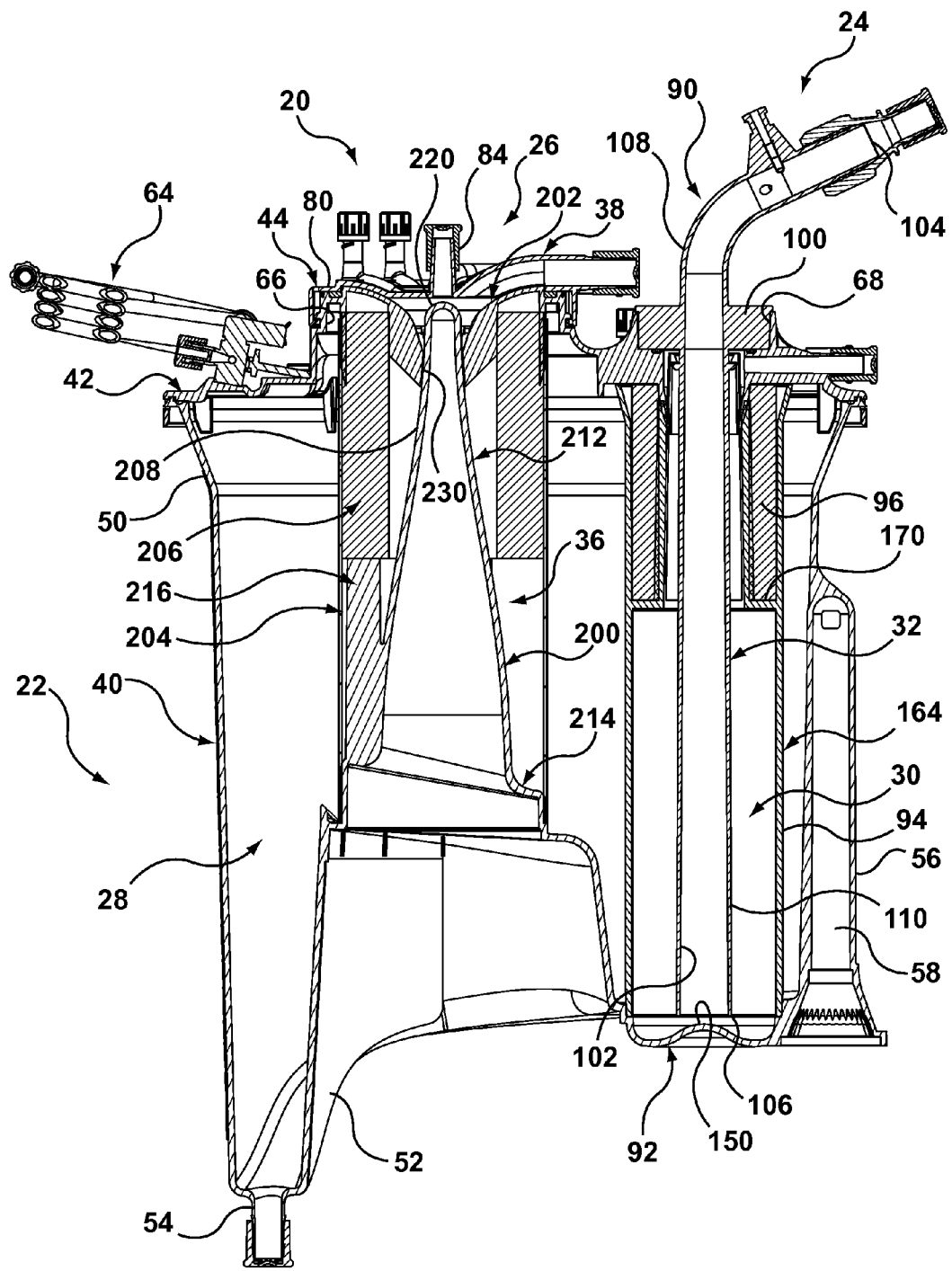
FIG. 1B is a cross-sectional view of the reservoir device of FIG. 1A.

An extracorporeal blood circuit reservoir 20 in accordance with principles of the present is disclosure shown in FIGS. 1A and 1B. The reservoir 20 includes a housing 22 and a venous inlet assembly 24. In some embodiments, reservoirs of the present disclosure can serve as a combined cardiotomy and venous reservoir, with FIGS. 1A and 1B reflecting an optional cardiotomy assembly 26. Details on the various components are provided below. In general terms, however, the housing 22 defines a main chamber 28. The venous inlet assembly 24 is maintained by the housing 22, and forms a venous chamber 30 through which venous blood flow from a venous downtube 32 is directed into the main chamber 28. One or more luer ports 34 extend from the venous downtube 32, and facilitate delivery of blood into the venous downtube 32 from other auxiliary circuit components. Where provided, the cardiotomy assembly 26 is also maintained by the housing 22, and establishes a cardiotomy chamber 36 through which cardiotomy blood flow from one or more cardiotomy inlet ports 38 is directed into the main chamber 28. Regardless of whether the cardiotomy assembly 26 is included, some aspects of the present disclosure relate to a relationship between the venous downtube 32 and the luer port(s) 34 that establishes a gentle, substantially non-turbulent merging of blood flow through the luer port(s) 34 with primary venous blood flow through the downtube 32. Apart from this relationship or arrangement of the luer port(s) 34 relative to the venous downtube 32, then, the reservoir 20 can assume a wide variety of other forms. For example, reservoir features useful with embodiments of the present disclosure are described in U.S. Publication No. 2010/0268148 (entitled "Cardiotomy and Venous Blood Reservoir and Method"), the teachings of which are incorporated herein by reference. Thus, the present disclosure is not limited to the housing 22, venous inlet assembly 24, or the cardiotomy assembly 26 as described below.

Figure 2:
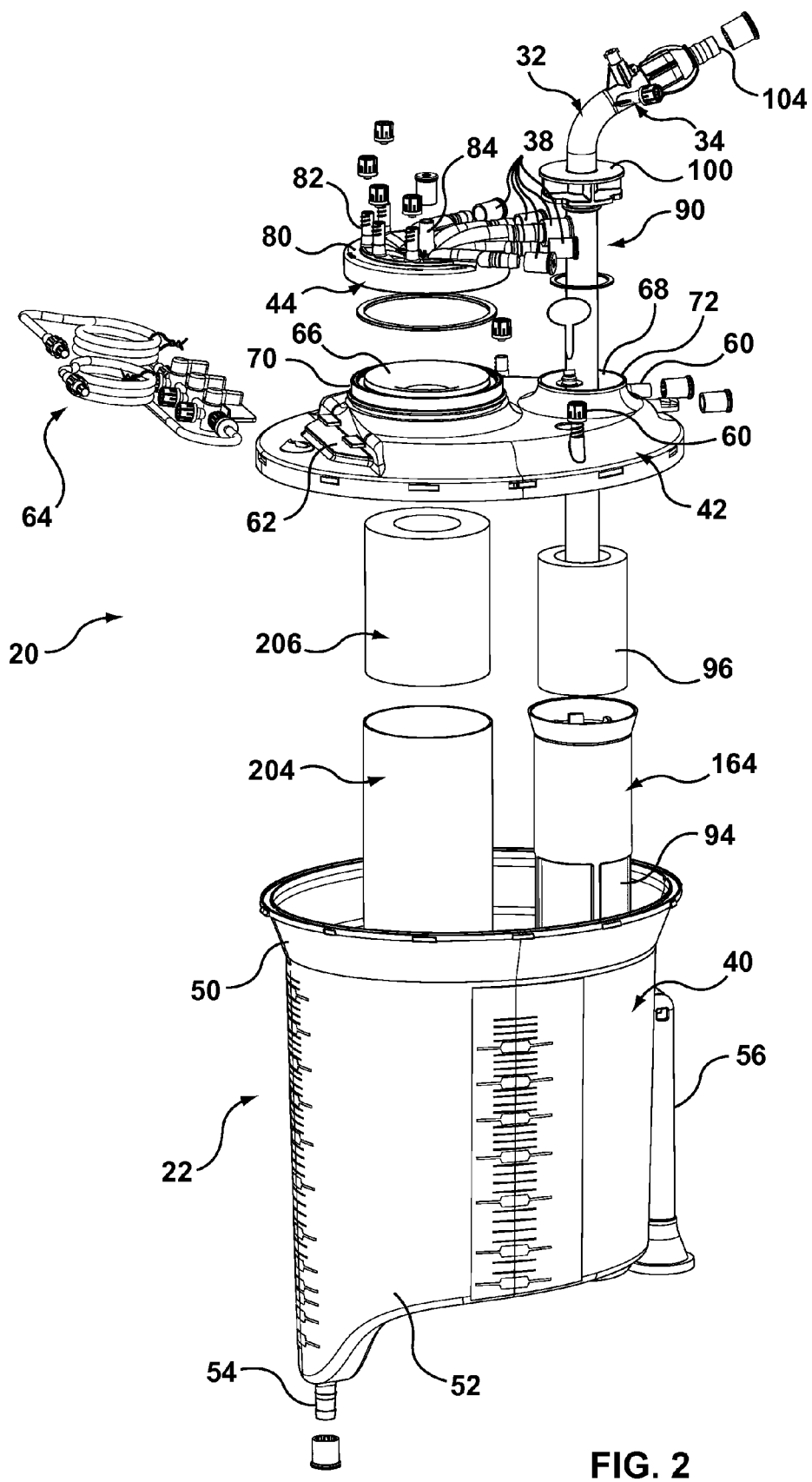
FIG. 2 is an exploded view of the reservoir device of FIG. 1A.

With additional reference to FIG. 2, the housing 22 can assume a variety of forms and in some embodiments includes a frame 40, a lid 42, and a turret 44. The frame 40 and the lid 42 combine to define the main chamber 28, with the lid 42 and the turret 44 maintaining one or more ports, such as the cardiotomy inlet port(s) 38.

The frame 40 is a hollow body defining an upper side 50 and a lower side 52. The lid 42 is assembled to the upper side 50, with the lower side 52 optionally having a contoured shape and terminating at an exit port 54 that is otherwise fluidly connected to the main chamber 28. While the frame 40 can have the generally cylindrical shape shown, other shapes are also acceptable, such as box-like. Optionally, the frame 40 forms a handle segment 56 sized for convenient grasping by a caregiver's hand. In related embodiments, the handle segment 56 is optionally configured to facilitate mounting of the reservoir 20 to a separate support structure (e.g., an upright post such as an IV stand), for example via a channel 58 formed through the handle segment 56.

The lid 42 is mounted to (or alternatively is formed as part of) the frame 40, and maintains or defines one or more connectors 60, such as a luer connector, ventilation connector, pressure relief valve housing connector, etc. Additional connectors can be formed or provided with the lid 42 and/or one or all of the connectors 60 illustrated can be omitted. Further, the lid 42 can form a bracket 62 configured to selectively receive and retain an optional tubing management assembly 64. Regardless, the lid 42 forms a first aperture 66 sized to rotatably receive the turret 44, and a second aperture 68 sized to rotatably receive a corresponding component of the venous assembly 24, as described below. In this regard, the first and second apertures 66, 68 are each circumscribed by a ridge 70, 72 (best shown in FIG. 2) optionally constructed to promote rotatable mounting of the turret 44 and the venous assembly component, respectively, relative to the lid 42.

The turret 44 includes, in some embodiments, a hub 80 maintaining a series of connectors, such as the cardiotomy inlet port(s) 38, a luer connector(s) 82, a prime connector 84, etc. More or fewer of the connectors can be provided with the turret 44 in other embodiments. Regardless, upon assembly of the turret 44 within the first aperture 66 of the lid 42, the turret 44 is rotatable relative to the lid 42 (and thus relative to the frame 40).

The lid 42 and/or the turret 44 can have constructions differing from those described above. For example, the rotational features are optional and can be omitted. In more general terms, the housing 22 serves to establish the main chamber 28, as well as flow paths or ports for venous and cardiotomy blood to the reservoir and a flow path or port of the treated blood from the reservoir 20.

The venous assembly 24 includes a venous inlet sub-assembly 90, a bowl 92, (FIG. 1B) a venous filter 94 (referenced generally in FIGS. 1B and 2), and a venous defoamer 96. In general terms, venous and other blood is directed from the venous inlet sub-assembly 90 to the bowl 92, and then to the venous filter 94. The venous defoamer 96 is positioned to interface with any foam associated with the blood accumulated within the bowl 92. More particularly, the bowl 92 and the venous filter 94, combine to define at least a portion of the venous chamber 30, with the venous defoamer 96 exposed to foam rising within the venous chamber 30.

The venous inlet sub-assembly 90 includes the downtube 32, the luer port(s) 34, and a mounting bracket 100. The mounting bracket 100 facilitates assembly of the venous inlet sub-assembly 24 with the second aperture 68 of the lid 42. The downtube 32 forms or defines a primary lumen 102 extending between, and open at, opposing inlet and outlet ends 104, 106. With these conventions in mind, the downtube 32 can be described as generally defining an inlet section 108 adjacent the inlet end 104 and an outlet section 110 adjacent the outlet end 106. Upon final assembly, the inlet section 108 is located external the housing 22, whereas the outlet section 110 is located within the housing 22.

Figure 3A:
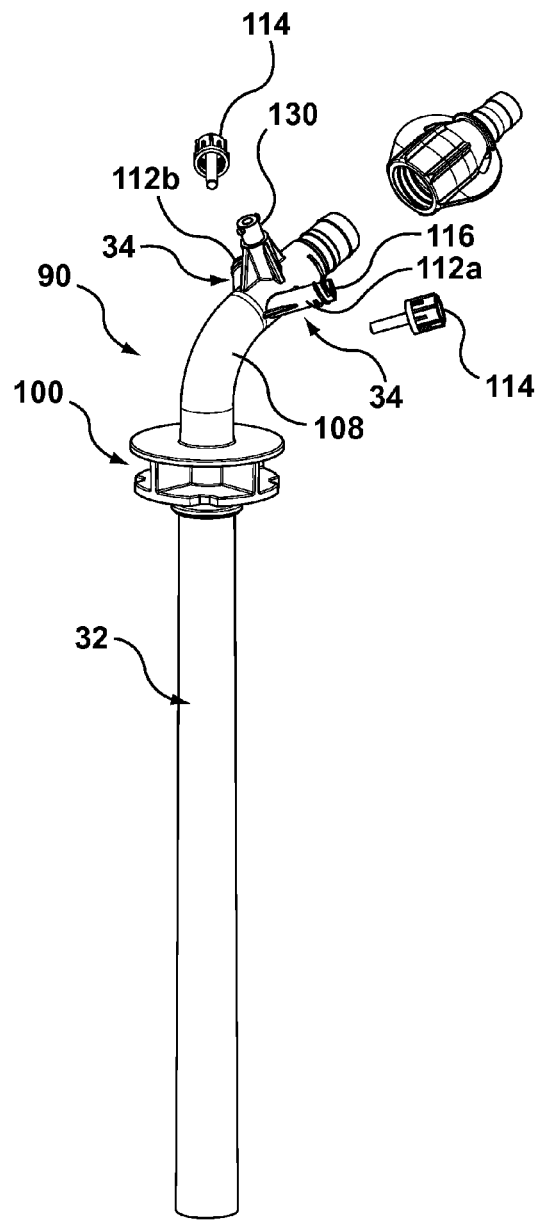
FIG. 3A is a perspective view of a venous inlet sub-assembly portion of the reservoir device of FIG. 1A.
Figure 3B:
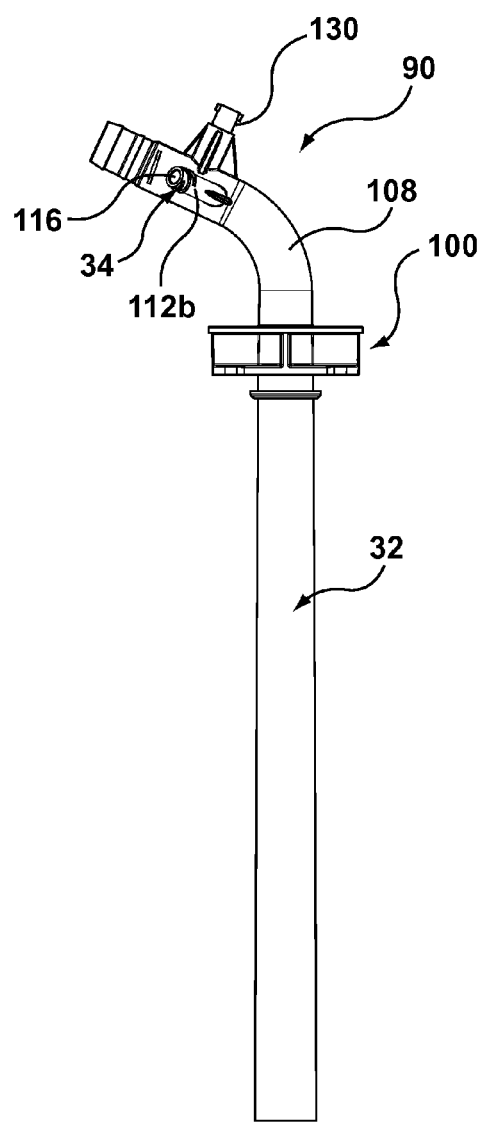
FIG. 3B is a side view of the sub-assembly of FIG. 3A with portions removed.
Figure 3C:
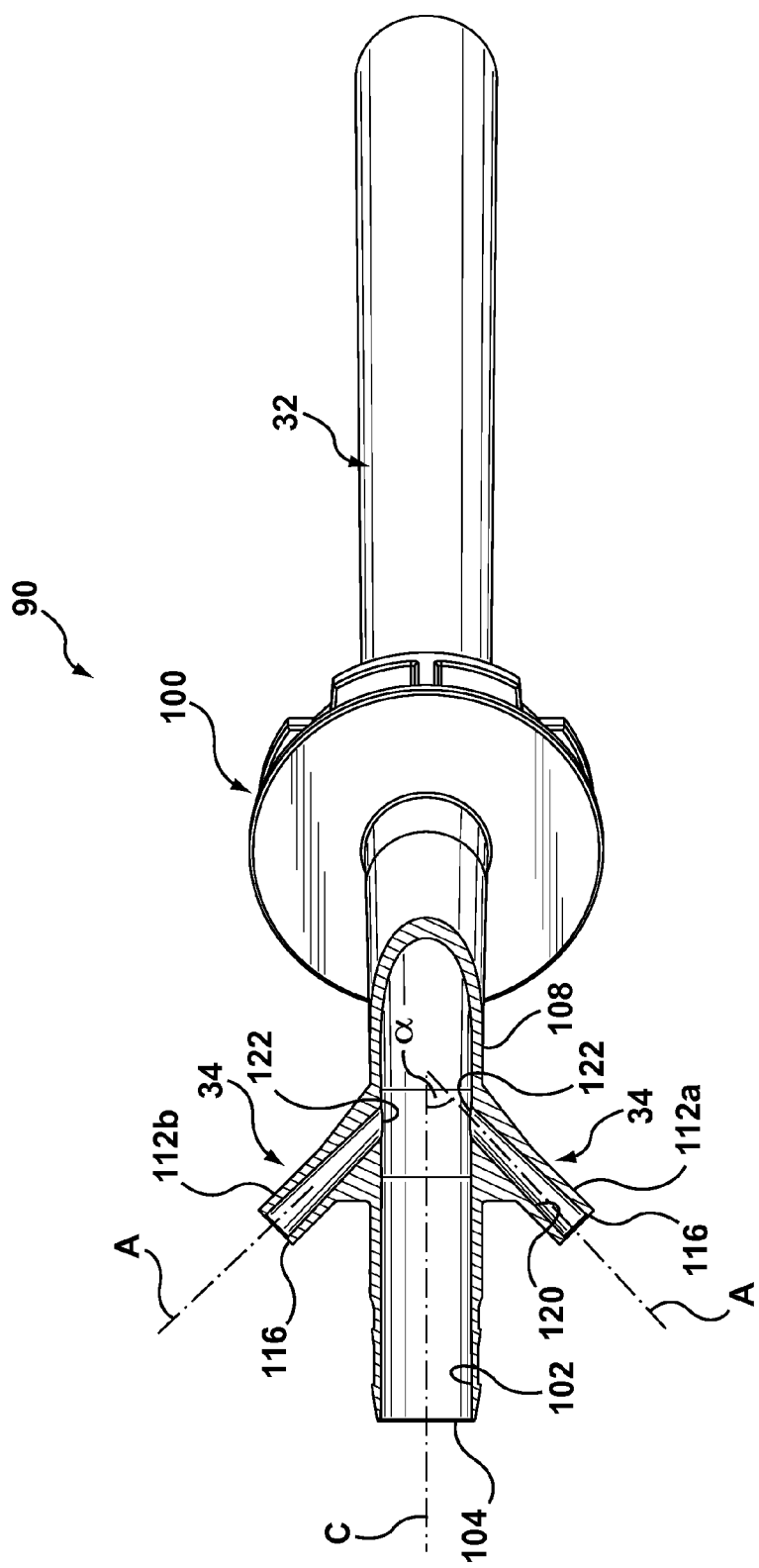
FIG. 3C is a cross-sectional view of the sub-assembly of FIG. 3A with portions removed.

The venous inlet sub-assembly 90, including the inlet section 108 of the downtube 32, is shown in greater detail in FIGS. 3A-3C. FIG. 3C more fully illustrates the downtube primary lumen 102 that is otherwise open at the inlet end 104. The primary lumen 102 defines a central axis C. At least along the portion of the inlet section 108 shown in FIG. 3C, the primary lumen axis C can be linear.

The luer port(s) 34 each include a connector body 112 and a luer adapter or fitting or lock 114 (omitted from the views of FIGS. 3B and 3C). As a point of reference, the venous inlet sub-assembly 90 reflected in FIGS. 3A-3C includes two of the luer port connector bodies 112a, 112b, although any other number, either greater or lesser, is also acceptable. Regardless, each of the port connector bodies 112a, 112b forms or defines a receiving end 116 configured for assembly to the corresponding luer adapter 114.

The luer port connector bodies 112a, 112b, and in particular a relationship or arrangement thereof relative to the downtube 32, can be identical, such that the following description of the first luer port connector body 112a applies equally to the second connector body 112b. With specific reference to FIG. 3C, the port connector body 112a has a tubular shape, and defines or forms an internal passageway 120. The passageway 120 is fluidly open to the primary lumen 102 of the downtube 32, for example via a flow opening 122 through a thickness of the wall of the downtube 32. Thus, fluid flow introduced into the port connector body 112a at the receiving end 116 is directed through the passageway 120 and into the primary lumen 102. In some embodiments, the connector body 112a, and thus the passageway 120, is entirely linear in extension from the downtube 32. Regardless, the flow opening 122 into the primary lumen 102 is formed downstream of the downtube inlet end 104, and an axial centerline A of the passageway 120 (at least at the flow opening 122) is non-perpendicular relative to the central axis C of the primary lumen 102 as reflected in FIG. 3C. Stated otherwise, an extension angle α is formed by an intersection of the axial centerline A with the central axis C. The extension angle α is less than 90°, and in some embodiments is in the range of 1°-85°; and in other embodiments is in the range of 15°-75°.

FIG. 3A illustrates that in some embodiments, the second port connector body 112b is circumferentially spaced from the first port connector body 112a. The angled non-perpendicular) relationship of the internal passageway 120 relative to the primary lumen 102 promotes non-turbulent merging of liquid flow from the port connector body 112a with existing, primary liquid flow in the primary lumen 102 (i.e., liquid flow delivered to the inlet end 104 and thus upstream of the port connector body flow opening 122). For example, FIG. 4A is a simplified, schematic illustration of liquid flow through the inlet section 108 of the downtube 32, as well as through the luer port connector bodies 112a, 112b. As a point of reference, when employed within an extracorporeal blood circuit, venous blood enters the primary lumen 102 at the inlet end 104 (referenced generally) with the arrow V in FIG. 4A representative of the venous blood (or primary) flow path along the primary lumen 102. Secondary blood flow (e.g., arterial filter purge flow) is directed into the luer port connector bodies 112a, 112b, as represented by the secondary flow path arrows $S_1$, $S_2$. As shown in FIG. 4A, the secondary flow paths $S_1$, $S_2$ enter the primary lumen 102 via the corresponding flow opening 122 at a non-perpendicular angle relative to the primary flow path V. This angled relationship reduces the possibility that the incoming, secondary blood flow along the secondary flow paths $S_1$, $S_2$ will induce turbulent flow into the venous blood moving along the primary flow path V.

While FIG. 4A reflects the luer port connector bodies 112a, 112b as being longitudinally aligned relative to the downtube 32 (i.e., the corresponding flow openings 122 are aligned), in other embodiments the luer port connector bodies 112a, 112b can be longitudinally offset. Similarly, while the luer port connector bodies 112a, 112b and corresponding internal passageways 120 are shown as being linear, in other embodiments one or more bends can be effectuated along a length of one or both of the luer port connector bodies 112a, 112b in extension from the downtube 32. With these alternative constructions, the non-perpendicular extension angle α (FIG. 3C) as defined by the port connector body axial centerline A is exhibited at least at the flow opening 122 as described above.

Figure 4B:
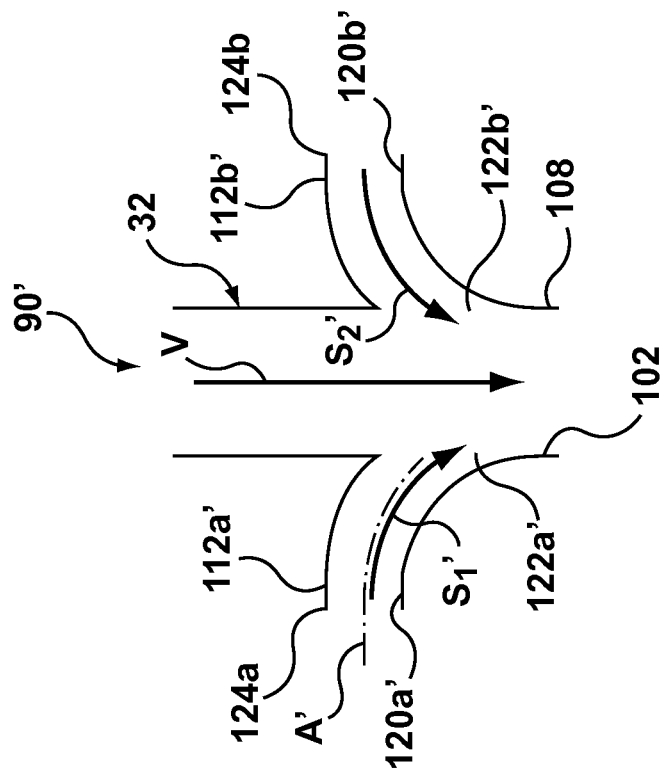
FIG. 4B is a schematic illustration of fluid flow through a downtube and luer ports of another inlet sub-assembly in accordance with principles of the present disclosure.
Figure 4A:
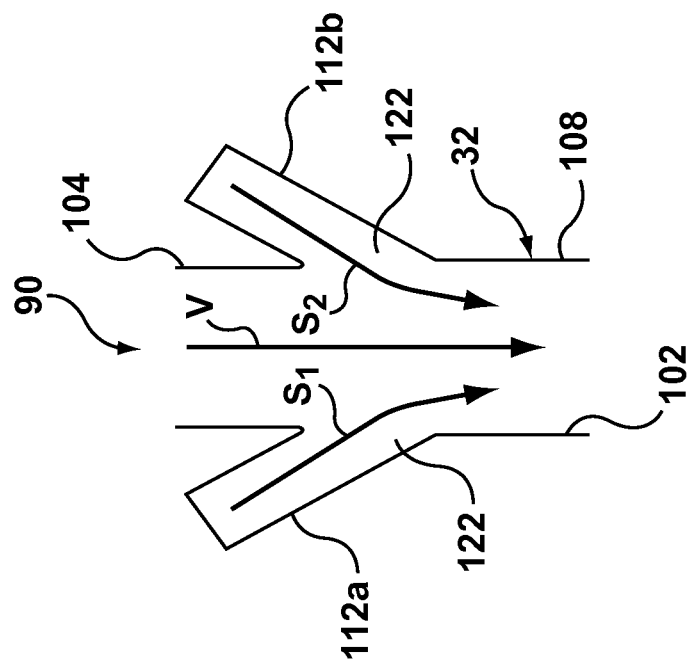
FIG. 4A is a schematic illustration of fluid flow through a downtube and luer ports of the inlet sub-assembly of FIG. 3A.

FIG. 4B schematically illustrates a portion of another embodiment venous inlet sub-assembly 90', including the inlet section 108 of the venous downtube 32 described above, along with first and second luer port connector bodies 112a', 112b'. The luer port connector bodies 112a', 112b' extend from the downtube 32, and each define an internal passageway 120a', 120b', fluidly open to the primary lumen 102 via a corresponding flow opening 122a', 122b'. With the construction implicated by FIG. 4B, the luer port connector bodies 112a', 112b' extend in a non-linear fashion from the downtube 32. Stated otherwise, an axial centerline A' defined by the internal passageways 120a', 120b' is non-linear or curved. With this construction, an entrance side 124a, 124b of the luer port connector bodies 112a', 112b' can be arranged substantially perpendicular to the central axis C (FIG. 3C) of the primary lumen 102. However, the luer port connector bodies 112a', 112b' are configured and arranged such that at the corresponding flow opening 122a', 122b' the corresponding axial centerline A' is angled or non-perpendicular relative to the primary lumen 102. As a result, secondary blood flow along the secondary flow paths $S_1'$, $S_2'$ gently merges with the venous blood flow along the primary flow path V, with minimal, if any, induced turbulent flow.

Returning to FIGS. 3A-3C, the venous inlet sub-assembly 90 can include additional ports projecting from the downtube 32. For example, a temperature sampling port 130 can be assembled to the downtube 32 adjacent the luer port connector bodies 112a, 112b. While the temperature sampling port 130 is fluidly open to the primary lumen 102, the corresponding internal passageway may or may not be arranged perpendicular to the primary lumen 102. Because the temperature sampling port 130 is not employed for delivering liquid flow into the primary lumen 102, the turbulent flow concerns addressed by the luer port connector bodies 112a, 112b does not exist. For example, a sheath (not shown) can be embedded into the temperature sampling port 130 that mates with the temperature probe (not shown) and fluidly isolates the temperature sampling port 130 from the primary lumen 102.

Returning to FIGS. 1A-2, remaining components of the venous assembly 24 can assume various forms that may or may not be implicated by the drawings. For example, the bowl 92 forms a floor surface 150 and in some constructions is an integrally formed component of the housing 22; alternatively, the housing 22 and the bowl 92 can be separately formed and subsequently assembled. The floor surface 150 serves to guide or direct venous blood flow within the venous chamber 30, such that the venous chamber 30 can be viewed as having an inlet at the outlet end 106 of the downtube 32 and an outlet at the venous filter 94. The floor surface 150 optionally forms the contoured regions reflected in FIG. 1B (e.g., an umbrella shape), although a variety of other shapes are also acceptable. With the one embodiment shown, a curvature of the bowl surface 150 is configured to direct bubbles upwardly through a tangential transition from the downtube 32 to the venous filter 94. This optional feature prevents or minimizes turbulent flow and maintains bubble integrity.

The venous filter 94 can assume a form commensurate with formats conventionally employed for venous blood filtering, such as a screen material (e.g., 105 micron screening). With some constructions, the venous filter 94 is a pleated screen, formed as an annular ring. The venous filter 94 can be assembled to a cage 164 that in turn is mounted to the bowl 92 as shown. The ring-shaped venous filter 94 can be generally cylindrical in shape or can have a tapered shape.

The venous defoamer 96 is formed of a material conventionally employed for venous blood defoaming (e.g., polyurethane foam) that is optionally coated with an anti-foaming agent such as simethicone. In some embodiments, the cage 164 is configured to retain to the venous defoamer 96 about the downtube 32 at a location longitudinally spaced from the downtube outlet end 106. Other configurations and arrangements of the venous defoamer 96 are also envisioned. For example, the venous defoamer 96 can be mounted directly to the downtube 32. In yet other embodiments, the venous defoamer 96 can be omitted.

With the above construction, venous blood flow into the downtube 32 is directed by the primary lumen 102 to the outlet end 106. The venous blood is then dispensed from the outlet end 106 and onto the floor surface 150 of the bowl 92. Venous blood accumulates within the bowl 92, with the floor surface 150 directing the venous blood flow to the venous filter 94 where appropriate filtration occurs prior to the venous blood entering the main chamber 28. As mentioned above, the optional umbrella-like shape of the bowl floor surface 150 minimizes turbulent flow and maintains bubble integrity as the blood flow transitions from the downtube 32 to the venous filter 94. A leading end 170 of the venous defoamer 96 is offset from the above-described venous blood flow path such that the venous blood does not unnecessarily interface with the venous defoamer 96. Instead, any foam associated with the venous blood within the venous chamber 30 will rise upwardly and only then contact the venous defoamer 96 to effectuate desired defoaming.

The cardiotomy assembly 26, where provided, is off-set from the venous assembly 24 in some embodiments. As best shown in FIG. 1B, the cardiotomy assembly 26 can include framework 200, a dish 202, a cardiotomy filter 204, and a cardiotomy defoamer 206. In general terms, the framework 200 maintains the cardiotomy filter 204 and the cardiotomy defoamer 206. The dish 202 directs cardiotomy liquid flow from the cardiotomy inlet port(s) 38 to the framework 200, with the framework 200, in turn, directing the cardiotomy liquid flow to the cardiotomy filter 204 via a guide surface 208. The filtered cardiotomy liquid is subsequently directed to the main chamber 28 as described below. Further, the cardiotomy defoamer 206 is positioned to selectively interface with primarily the foam portion of the cardiotomy liquid delivered to, and maintained by, the cardiotomy chamber 36.

The framework 200 can assume a variety of forms and in some constructions includes an inner post 212, a floor 214, and an outer frame 216. The inner post 212 can have the generally cylindrical shape as shown, gradually increasing in diameter from a leading end 220 to the floor 214. The leading end 220 can be rounded to promote non-turbulent flow of liquid from the dish 202, and the outer guide surface 208 of the post 212 is smooth. The framework 200 can be integrally and homogenously formed with the housing 22, or can be separately formed and subsequently assembled to the housing 22.

The floor 214 extends radially outwardly and downwardly from the inner post 212, and in some constructions is adapted to maintain a portion of the cardiotomy filter 204. The floor 214 can assume the angled format reflected in FIG. 1B, defining a general flow direction toward the venous assembly 24. Alternatively, other shapes and/or flow directions are also acceptable.

The outer frame 216 extends from the floor 214 opposite the inner post 212, and is constructed to support and maintain and the cardiotomy defoamer 206. Also, the outer frame 216 can assist in supporting the cardiotomy filter 204.

The cardiotomy filter 204 can be of a type conventionally employed for cardiotomy blood filtration and thus can be a felt material (e.g., 30 micron depth or mesh filter). In some constructions, the cardiotomy filter 204 is a pleated depth or mesh filter, formed as a ring and circumscribing the framework 200.

The cardiotomy defoamer 206 is also of a type conventionally employed for cardiotomy liquid defoaming (e.g., polyurethane foam), and is assembled to the framework 200 so as to be spaced from the floor 214. With this construction, flow of cardiotomy liquid along the floor 214 need not necessarily interface with the cardiotomy defoamer 206.

The dish 202 can have a funnel-like shape, and forms a central aperture 230 (referenced generally). The central aperture 230 is coaxially disposed about the inner post 212, and is configured to direct cardiotomy liquid flow from the cardiotomy inlet port(s) 38 to the guide surface 208 via the aperture 230. Upon final construction, the inner post 212 and the cardiotomy filter 204 combine to at least partially define the cardiotomy chamber 36, with the guide surface 208 and the floor 214 defining a flow path through the cardiotomy chamber 36.

More particularly, cardiotomy liquid entering the reservoir 20 via the cardiotomy inlet port(s) 38 is directed by the dish 202 to the inner post 212. The cardiotomy liquid transfers from the dish 202 to the guide surface 208 via the central aperture 230. The cardiotomy liquid flows (via gravity) along the guide surface 208 to the cardiotomy filter 204. Any foam associated with the cardiotomy liquid otherwise accumulating along the guide surface 208 "behind" the cardiotomy filter 204 rises upwardly and into contact with the cardiotomy defoamer 206. The cardiotomy liquid is subsequently filtered by the cardiotomy filter 204, and then is directed into the main chamber 28 for more complete mixing with the filtered venous blood. FIG. 1B thus reflects that the cardiotomy filter 204 is disposed within the housing 22 fluidly between a cardiotomy outlet at the aperture 230 and the exit port 54.

The cardiotomy assembly 26 can differ in construction or format from the descriptions above. For example, the cardiotomy assembly 26 can have a stacked construction relative to the venous assembly 24. In yet other embodiments, the cardiotomy assembly is entirely omitted.

Figure 5:
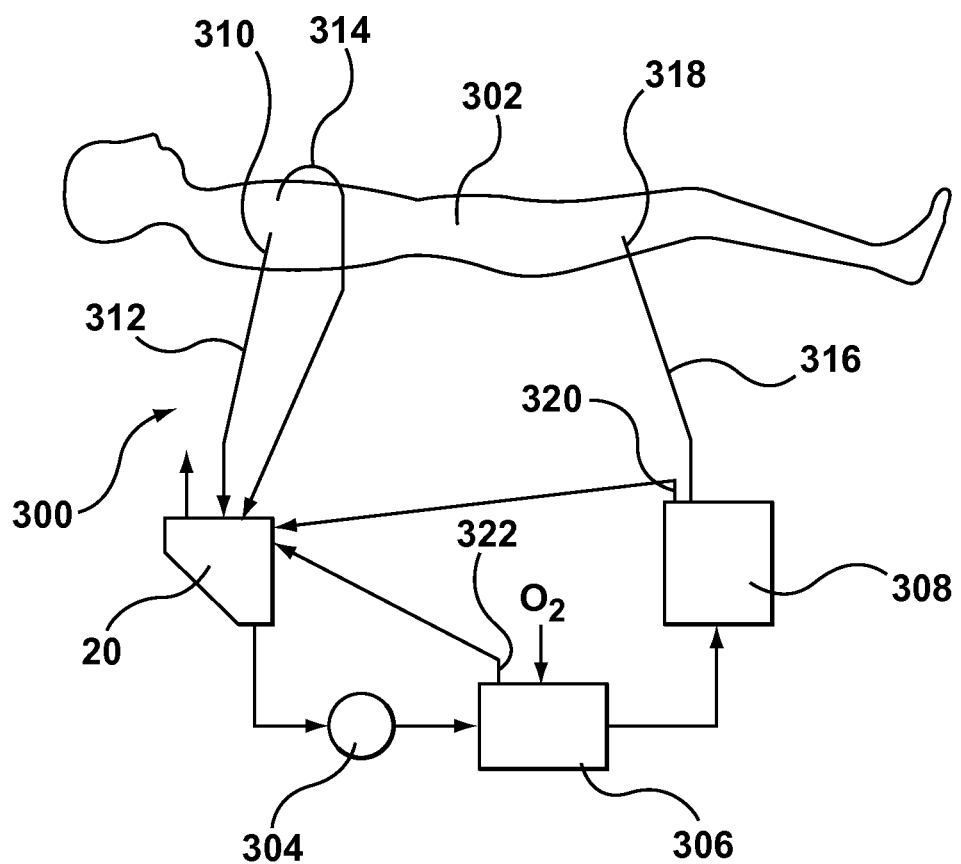
FIG. 5 is a schematic drawing of a cardiopulmonary bypass circuit including the reservoir device of FIG. 1A.

Regardless of whether the reservoir 20 incorporates the cardiotomy assembly 26, the reservoir 20 can be incorporated into an extracorporeal blood circuit 300 as generally shown in FIG. 5. The circuit 300 is connected to a patient 302, and generally includes a pump 304, an oxygenator 306, and an arterial filter 308. A venous cannula 310 (referenced generally) delivers venous blood from the patient 302 to the reservoir 20 via a venous line 312. A cardiotomy line 314 directs cardiotomy flow either directly to the reservoir 20, or to a separate cardiotomy reservoir, the output of which is delivered to the reservoir 20. Regardless, the pump 304 controls blood flow from the reservoir 20 to the oxygenator 306 (that may or may not incorporate heat exchange features). Finally, oxygenated blood flow is directed from the oxygenator 306 to the arterial filter 308 and then back to the patient 302 via a return line 316 and arterial cannula 318. With cross-reference between FIGS. 1B and 5, the venous line 312 is fluidly coupled to the inlet end 104 of the venous downtube 32. A purge port 320 provided with the arterial filter 308 is fluidly connected one of the luer ports 34. In this regard, the purge port 320 can be directly connected to the selected luer port 34. Alternatively, a sampling manifold (not shown) can be provided. An arterial line of the sampling manifold is connected to the arterial filter purge port 320, and a venous line of the sampling manifold is connected to the selected luer port 34. Other components of the circuit 300 can also be connected to a selected one of the luer ports 34. For example, FIG. 5 reflects a purge port 322 associated with the oxygenator 306 being fluidly connected to a second one of the luer ports 34 (either directly or via an optional sampling manifold). Alternatively, other auxiliary equipment (e.g., hemoconcentrator) can be connected to a selected one of the luer ports 34. In yet other applications, one of more of the available luer ports 34 are unused and thus fluidly closed.

During operation of the extracorporeal blood circuit 300, venous blood flow from the patient 302 enters the downtube 32, and is combined with auxiliary blood flow entering the downtube 32 via the selected luer port(s) 34. Due to the angled (i.e., non-perpendicular) arrangement of the corresponding luer port connector body 112 relative to the primary lumen 102 of the downtube 32, merging of the auxiliary blood flow with the venous blood flow within the downtube 32 causes minimal, if any, turbulence. As a result, gross air bubbles carried by the venous blood flow into the downtube 32 are not overtly disrupted, and are readily removed from the reservoir 20. In general terms, the gross air bubbles float to the surface of the liquid in the reservoir 20 (e.g., within the venous chamber 30) and dissipate into the atmosphere via a vent. The angled luer port connector bodies 112 minimize occurrences of gross air bubble disruption into more difficult to remove GME. Overall GME performance of the reservoir 20 is enhanced, and allows for the implementation of a larger pore size venous filter 94 that in turn minimizes blood trauma (and can also reduce dynamic holdup).

Figure 6:
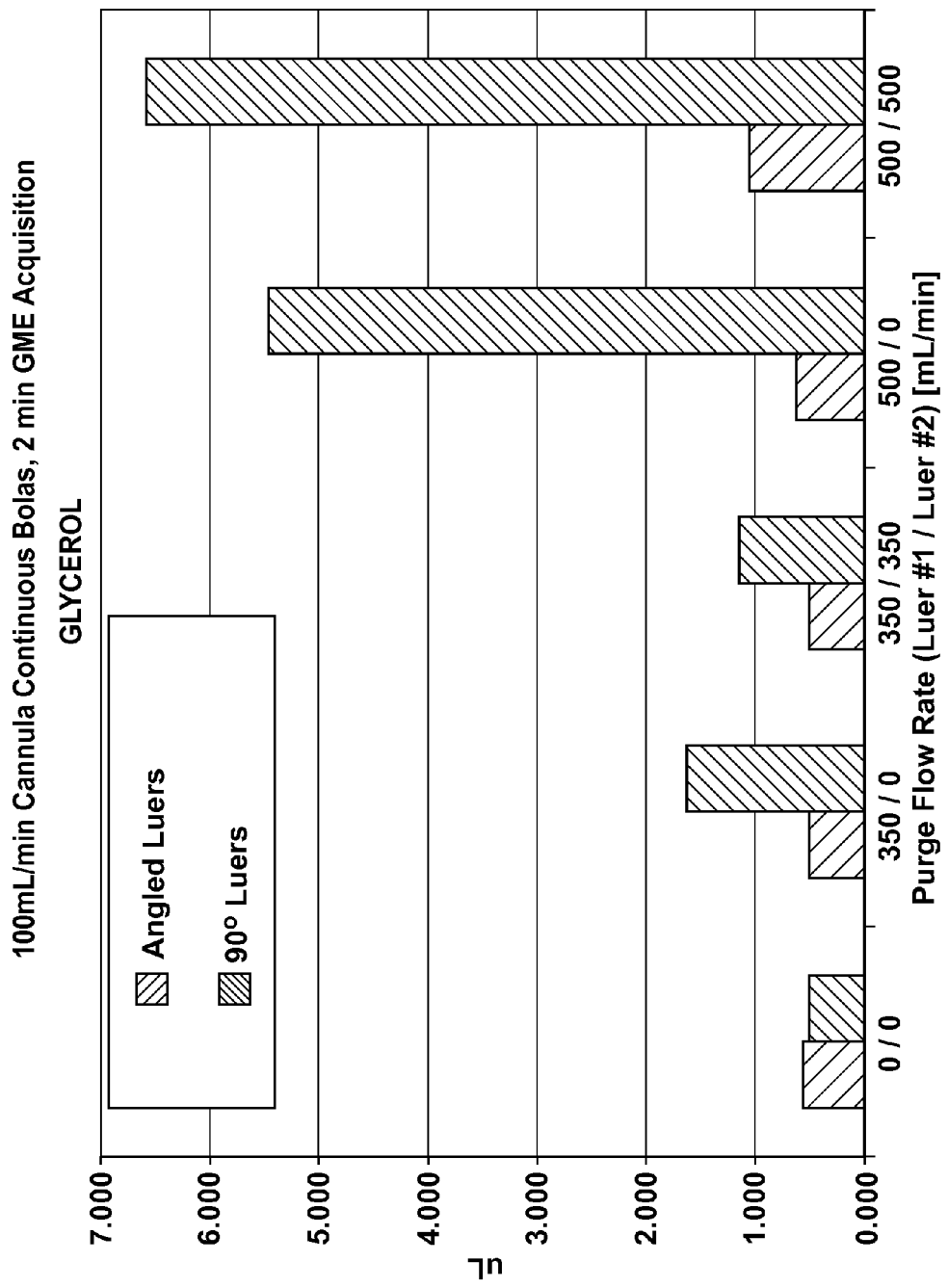
FIG. 6 is a chart showing test results.

Testing was performed to evaluate the performance of the angled luer ports of the present disclosure as compared to conventional constructions in which the luer ports are entirely perpendicular to the corresponding venous downtube. In particular, reservoirs were constructed in accordance with the configuration of FIG. 1B, as were comparative reservoirs having effectively identical construction except that the luer ports were arranged at a 90° angle relative to the venous downtube lumen. The sample and comparative reservoirs were subjected to testing parameters in which a continuous bolus of air at 100 mL/min was delivered to the downtube with a glycerol flow rate of 4.5 L/min. Further, glycerol was continuously delivered to one or both of the luer ports at various flow rates. Over the course of a two minute testing period, the amount of air (microliter) passing through the venous filter was measured and recorded. The results of the tests are shown in FIG. 6. As illustrated, larger volumes of air (passing through the venous filter) were found with the perpendicular luer port comparative examples then were evidenced with the angled luer port construction of the present disclosure. For example, where auxiliary liquid flow was introduced into both luer ports at a rate of 500 mL/min., more than six times the amount of air passed through the venous filter of the conventional or comparative example reservoir as compared to the sample reservoir incorporating the angled luer ports. This finding is indicative of gross air bubbles otherwise carried by the primary liquid flow through the venous downtube being subjected to turbulence, reduced in size (e.g., GME), and thus is able to pass through the venous filter.

Other embodiments of the present disclosure provide one or more optional components with the venous assembly 24 (FIG. 1B) that may enhance dynamic holdup performance of the reservoir. As a point of reference, for dynamic holdup, the primary goal is to reduce the volume of blood not available to the perfusionist while blood is flowing through the reservoir. For the venous portion of the reservoir, this is defined as the volume of blood that is held up by the venous filter or screen when operating at a high flow rate (e.g., 7 L/min), or more simply it is the volume of fluid within the venous chamber (or the venous cage) that is above the fluid level in the reservoir/main chamber.

Figure 7:
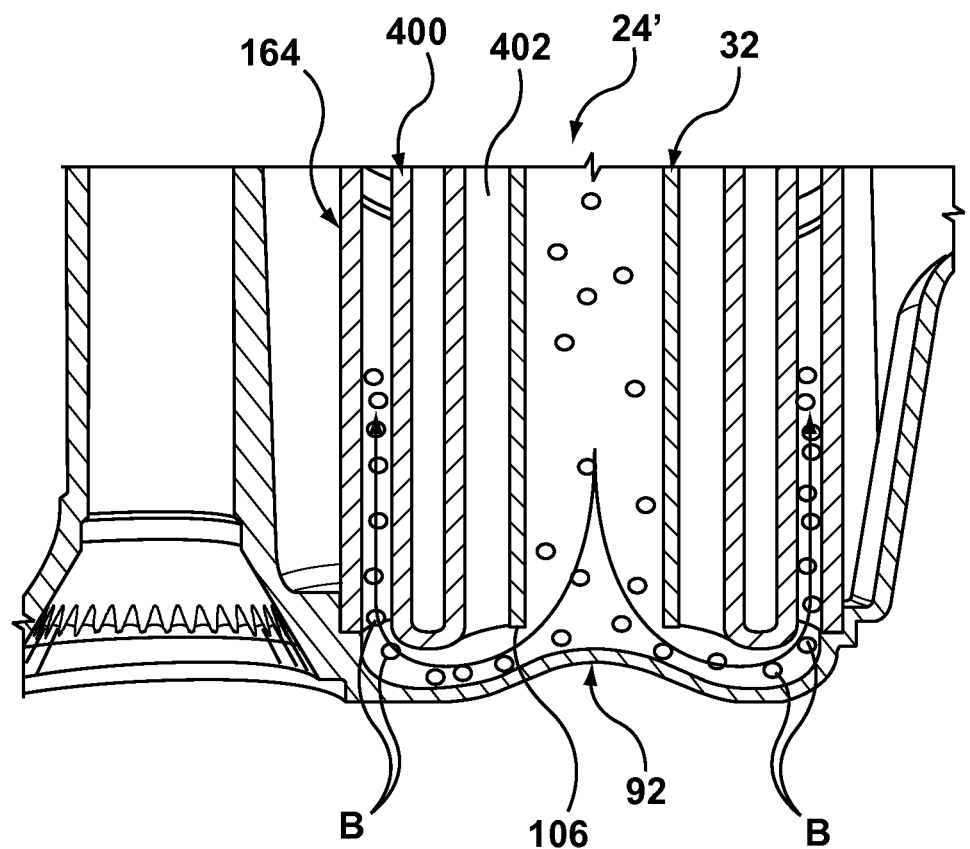
FIG. 7 is a simplified, cross-sectional view of an alternative reservoir device in accordance with principles of the present disclosure.

With the above in mind, FIG. 7 illustrates a portion of an alternative venous assembly 24' useful with reservoirs of the present disclosure. The venous assembly 24' is akin to the venous assemblies described above, and includes the downtube 32, the bowl 92, and the cage 164 (that otherwise supports a venous filter (not shown)). In addition, a volume displacer 400 is formed about the downtube 32, extending proximally from the downtube outlet end 106. The volume displacer 400 is a solid, tubular body, and is radially spaced from the cage 164 (and then from the venous filter carried thereby). A recirculation pathway 402 is optionally defined between the downtube 32 and the volume displacer 400 (and is otherwise in fluid communication with a recirculation port (not shown)). Alternatively, the volume displacer 400 can directly abut the downtube 32. Regardless, the volume displacer 400 essentially reduces the open volume between the downtube 30 and the cage 164 (i.e., were the volume displacer 400 is not present, the available space or volume would be greater). With this arrangement, volume displacer 400 improves dynamic holdup at virtually all reservoir liquid levels and does not cause turbulent flow. As reflected in FIG. 7, the volume displacer 400 directs air bubbles B to the surface of the venous filter (otherwise retained by the cage 164). The flow path of bubbles B directly to the surface of the venous cage could be further enhanced by adding vanes to the volume displacer 40 that would otherwise prevent the bubbles B from circulating in turbulent flow. Regardless, the volume displacer 400 serves to accelerate the bubbles B to the surface (higher fluid velocities with lower cross-sections) before they can break up into GME.

The reservoirs of the present disclosure provide a marked improvement over previous designs. By incorporating angled luer ports with the venous downtube, reservoirs of the present disclosure reduce turbulent flow within the downtube when a continuous purge or bolus is run through the corresponding luer port, thereby resulting in superior GME performance.

Although the present disclosure has been described with reference to preferred embodiments, workers skilled in the art will recognize that changes can be made in form and detail without departing from the spirit and scope of the present disclosure.

What is claimed is:

1. An extracorporeal blood circuit reservoir device comprising:
   a housing defining a main chamber;
   an exit port fluidly connected to the main chamber;
   a venous inlet sub-assembly mounted to the housing and including:
   a downtube forming a primary lumen extending between and open at opposing inlet and outlet ends, the downtube defining an inlet section adjacent the inlet end and an outlet section adjacent the outlet end,
   a first luer port connector body extending from the inlet section and forming a passageway open to the primary lumen at a flow opening,
   wherein the port connector body is arranged relative to the inlet section such that a flow path of fluid flow from the passageway into the primary lumen merges with a flow path of fluid flow along the primary lumen at an angle of less than 90°;
   wherein the venous inlet sub-assembly is arranged to locate the inlet section and the port connector body outside of the housing and the outlet section within the housing; and
   a venous filter maintained within the housing fluidly between the outlet end and the exit port.

2. The reservoir device of claim 1, wherein an extension angle defined at an intersection of an axial centerline of the passageway with a central axis of the primary lumen is less than 90°.

3. The reservoir device of claim 2, wherein the extension angle is in the range of 1°-85°.

4. The reservoir device of claim 2, wherein the axial centerline is linear along an entire length of the port connector body.

5. The reservoir device of claim 2, wherein the axial centerline is non-linear along a length of the port connector body.

6. The reservoir device of claim 1, further comprising a luer lock assembled to the port connector body.

7. The reservoir device of claim 1, wherein the venous inlet sub-assembly further includes:
   a second luer port connector body extending from the inlet section and forming a passageway;
   wherein the second port connector body is arranged relative to the inlet section such that a flow path of fluid flow from the passageway of the second port connector body into the primary lumen merges with a flow path of fluid flow along the primary lumen at an angle less than 90°.

8. The reservoir device of claim 7, wherein the passageway of each of the port connector bodies defines an axial centerline, and further wherein an intersection of each of the axial centerlines with a central axis of the primary lumen forms an extension angle of less than 90°.

9. The reservoir device of claim 7, wherein the second port connector body is circumferentially spaced from the first port connector body.

10. The reservoir device of claim 7, wherein the first port connector body is longitudinally aligned with the second port connector body.

11. The reservoir device of claim 7, wherein the venous inlet assembly further includes a sampling port body extending from the inlet section and fluidly open to the primary lumen.

12. The reservoir device of claim 1, further comprising:
a bowl disposed within the housing and forming a floor surface arranged to receive fluid flow from the downtube outlet end;
wherein the floor surface defines a curvature adapted to tangentially transition the fluid flow from a central region of the floor surface to a radially outward region of the floor surface.

13. The reservoir device of claim 1, further comprising:
a cardiotomy inlet assembly mounted to the housing and defining a cardiotomy inlet and a cardiotomy outlet; and
a cardiotomy filter disposed within the housing fluidly between the cardiotomy outlet and the exit port.

14. The reservoir device of claim 13, wherein the venous filter and the cardiotomy filter are arranged to guide fluid flow into the main chamber.

15. The reservoir device of claim 1, wherein arrangement of the first port connector body relative to the downtube is configured such that at a port flow rate of less than 500 mL/minute through the passageway, fluid flow from the first port connector body does not induce turbulent flow into fluid flowing through the primary lumen.

16. An extracorporeal blood circuit comprising:
a venous cannula for cannulation to a patient and receiving venous blood;
a reservoir device including:
a housing defining a main chamber,
an exit port fluidly connected to the main chamber,
a venous inlet sub-assembly mounted to the housing and including:
a downtube forming a primary lumen extending between an opening at opposing inlet and outlet ends, the downtube defining an inlet section adjacent the inlet end and an outlet section adjacent the outlet end,
a luer port connector body extending from the inlet section and forming a passageway open to the primary lumen,
a venous filter maintained within the housing fluidly between the outlet end and the exit port;
wherein the venous cannula is fluidly connected to the inlet end of the downtube;
an arterial filter device including a purge port, wherein the arterial filter device is fluidly connected to the exit port downstream of the reservoir device, and further wherein the purge port is fluidly connected to the port connector body; and
an arterial cannula for cannulation to a patient downstream of the arterial filter;
wherein a primary venous flow path is established from the venous cannula and through the downtube, and a secondary flow path is established from the purge port and through the first port connector body, and further wherein the secondary flow path merges with the primary venous flow path within the inlet section at an angle less than 90°.

17. The circuit of claim 16, wherein an extension angle defined at an intersection of an axial centerline of the passageway with a central axis of the primary lumen is less than 90°.

18. A method of collecting and treating extracorporeal blood of a patient during surgical procedure, the method comprising:
directing venous source blood from the patient into an inlet end of a downtube having an outlet end;
directing secondary source blood into the downtube via a luer port connector body at a location upstream of the outlet end, including the secondary source blood flow merging with the venous source blood flow at an angle of less than 90°;
dispensing a combination of the venous source blood and the secondary source blood from the outlet end into a reservoir chamber; and
guiding the combination blood through a venous filter within the chamber.

19. The method of claim 18, further comprising:
directing blood from the reservoir to an arterial filler;
directing blood from the arterial filter back to the patient; and
purging a partial flow of blood from the arterial filter to the downtube as the secondary source blood.

20. The method of claim 18, wherein an arrangement of the connector port body relative to the downtube is configured such that at a secondary source blood flow rate of less than 500 mL/minute through the luer port connector body, the secondary source blood flow does not induce turbulent flow into the primary venous source blood flow.

* * * * *